United States Patent

Burgess

[11] Patent Number: 5,837,270
[45] Date of Patent: Nov. 17, 1998

[54] TOPICAL ANTI-ACNE COMPOSITION

[76] Inventor: Nelson Leon Burgess, 120-8E Einstein Loop North, Bronx, N.Y. 10475

[21] Appl. No.: 697,468

[22] Filed: Aug. 26, 1996

[51] Int. Cl.$^6$ ............................... A61K 9/06; A61K 9/10
[52] U.S. Cl. ................. 424/401; 424/195.1; 424/74; 424/78.03; 424/70.11; 424/70.12; 424/642; 514/937; 514/787; 514/859
[58] Field of Search ................ 424/401, 195.1, 424/74, 78.03, 70.11, 70.12, 642; 514/937, 787, 859

[56] References Cited

U.S. PATENT DOCUMENTS 4,569,839  2/1986  Grollier et al. ................. 424/195.1
4,614,652  9/1986  Vályi et al. ..................... 424/195.1
4,803,069  2/1989  Kékesi et al. ................... 424/195.1

OTHER PUBLICATIONS

Budavari, S., et al. (1989). The Merck Index. Merck & Co., Inc., pp. 336 and 1599.

*Primary Examiner*—Raj Bawa
*Attorney, Agent, or Firm*—Michael I. Kroll

[57] ABSTRACT

The present invention relates to a topical anti-acne formulation comprising, in a pharmaceutically acceptable carrier, a compound of the formula $C_6H_2ClOHR^1R^2$, wherein $R^1$ and $R^2$ are each independently C1 to C7 alkyl, C3 to C7 cycloalkyl or C3 to C7 aryl, and zinc oxide. The preferred formulation contains 4-chloro-3,5-dimethylphenol and zinc oxide.

1 Claim, 3 Drawing Sheets

TOPICAL ANTI-ACNE COMPOSITION

BACKGROUND OF THE INVENTION

Field of the Invention

The present invention relates to the field of treating the skin condition known as acne. More specifically, the present invention is concerned with the prophylactic or therapeutic topical treatment of acne. Even more specifically, the present invention is concerned with the topical treatment of such skin disorders as acne vulgaris, other acneiform dermal disorders, e.g. preadolescent acne, acne rosacea (now known as rosacea), premenstrual acne, acne venenata, acne cosmetica, acne detergicans, acne cosmetica, acne excoriee, gram negative acne, steroid acne, acne conglobata, or nodulocystic acne. The present invention can also be used for topically treating certain other types of acneiform dermal disorders, e.g. perioral dermatitis, seborrheic dermatitis in the presence of acne, gram negative folliculitis, sebaceous gland dysfunction, hiddradenitis suppurativa, pseudo-folliculitis barbae, or folliculitis.

The present invention relates to topically applied medicinal compositions and more particularly refers to such compositions having, as active topical medicinal ingredients, zinc oxide and a compound of the formula $C_6H_2ClOHR^1R^2$, wherein $R^1$ and $R^2$ are each independently C1 to C7 alkyl or C3 to C7 cycloalkyl or aryl.

Description of the Prior Art

Acne vulgaris is a common disease which afflicts approximately 90% of all teenagers and, not uncommonly, affects men and women in their twenties or thirties or may persist in adults for many years. Acne vulgaris most commonly occurs on oily areas of the skin with high sebaceous gland concentration. The areas of high sebaceous gland concentration are the face, ears, retroauricular areas (e.g. behind the ears), chest, back and occasionally the neck and upper arms.

Acneiform eruptions can occur wherever there is a pilosebaceous unit or sebaceous follicle which does include the entire surface of the skin. The basic lesion in acne is the comedo commonly known as the blackhead. The comedo is created by retention of layers of dead skin known as keratin in the lining of the follicles. In addition to hyperkeratosis (which is thickening or retentative layering of keratin), there is an accumulation of sebum which is the lipid-laden product of the sebaceous gland. The cells of the sebaceous glands in which sebum originates are the sebocytes. The combination of the keratin and the sebum produces a plugging of the mouth or opening of the follicular canal and papules are formed by inflammation around the comedones (plural of comedo). Depending upon the degree of inflammation, pustules, cysts, nodules, granulomatous reactions, scars and keloids may develop.

Most typical forms of mild acne vulgaris demonstrate the predominance of comedones with the occasional pustules. Pustules and papules predominate in more severe cases. These can heal with scar formation; that is, fibrosis of the lesions which are deep and penetrating. In moderately active cases, larger cystic lesions can develop.

Acne vulgaris can appear in many clinical varieties. The mildest case manifests comedones on oily skin and is called acne comedo.

Papular acne is another variety of acne which has many inflammatory papules.

This form of acne is common in adolescent skin, but it can be seen in all ages. The papular inflammatory form of acne can progress to an indurated, deeper and destructive form known as acne indurata. These lesions can produce severe scarring and can be quite deep seated and destructive.

Steroid acne vulgaris can occur when oral corticosteroids or topical steroids are used and occurs as inflammatory follicular papules. When oral corticosteroids are ingested, the inflammatory papules are usually sudden in appearance and can cover the chest, back, arm and face. When topical corticosteroids are used for more than two weeks, a localized inflammatory apular response can develop which can proceed to a granulomatous chronic reaction known as steroid acne rosacea.

Premenstrual acne can occur in a large number of menstruating women as a papular and pustular acne vulgaris, approximately one week prior to menstruation. There is a body of evidence that implicates a surge in progesterone as the mediator of premenstrual acne.

Preadolescent acne is divided into neonatal, infantile and childhood forms of acne. The neonatal form is limited to the first few weeks of life. It usually develops a couple of days after birth. It more commonly afflicts males and reveals transient facial papules and pustules which can clear spontaneously in a few days or weeks. The stimulation of neonatal sebaceous glands by circulating maternal progesterone appears to be the cause.

If the acne persists beyond the first month of life, the acne is called infantile acne and can extend into childhood, adolescence and adult life. The childhood acne can result from a persistent infantile acne or can develop de novo after age two. This form of acne is uncommon, but it has more of a male predilection. It is characterized by comedones commonly in groups, papules, pustules and, rarely, cysts. This condition can extend from a few weeks to several years and can develop into pubertal acne.

Acne venenata is by definition a comedonal or papular acne which occurs after exposure to chlorinated hydrocarbons (chloracne), cutting oils, petroleum oil, coal tar and pitches.

Acne cosmetica is a persistent low grade comedonal and/or papular and pustular acne that occurs usually on the chin and cheeks of adult women due to oil-based cosmetics, i.e. foundations, facial creams and sunscreens.

Acne detergicans occurs as a type of comedonal acne in patients who use oil-based cleansing soaps. Acne excoriee, also known as pickers acne, starts out as a mild form of papular or comedonal acne which is manipulated or picked and causes further inflammation, more papules and sometimes scars, pitting and atrophy of the skin.

Gram negative acne, sometimes called gram negative folliculitis when it extends to the neck, arms, legs and trunk, is a form of an inflammatory papular, follicular and pustular response to gram negative organisms including Enterobacter, Klebsiella, Escherichia, Proteus, Serratia and Pseudomonas. The most characteristic lesion on the face are superficial pustules, or papulo-pustules (which is a combination of a papule and pustule). The face can show diffuse erythema and inflammation surrounding these pustules and juicy papules or papulo-pustules.

The gram negative acne is usually highly resistant and usually occurs in patients who have bad inflammatory papular acne for long periods or who have been treated with long term oral administration of antibiotics such as tetracycline, erythromycin, or minocycline or topical antibiotics such as topical clindamycin or topical erythromycin. Subsequent to the oral administration of tetracycline or erythromycin, oral administration of amoxicillin, ampicillin and trimethoprim-sulfomethoxazole has been shown to be effective in treating this disease.

Acne rosacea is an inflammatory eruption that is chronic and occurs on the face, especially on the nose as well as the scalp and neck, in some instances. It is manifested by erythema, pustules, papules, telangiectasia (which is dilation of superficial capillaries) and hypertrophy of sebaceous glands. The middle portions of the face are most frequently involved. The eyes and eyelids are not uncommonly involved and can produce inflammation and infection of the conjunctiva, eyelids and hypertrophy of the meibomian glands. Acne rosacea is often called simply rosacea and is most common in middle aged women and men. Rosacea can go on to form a granulamatous rosacea which is characterized by resistant inflammatory papules which when biopsied reveal non-caseating epithelial cell granulomas.

Pseudofolliculitis barbae is a predominantly male affliction which is characterized by inflammatory papules and pustules on the bearded area of the face. The mechanism is thought to be an inflammatory response to the end of hair (usually curly beard facial hair) into the skin causing a foreign body inflammatory response.

Folliculitis is an inflammatory reaction around the hair follicle which can be bacterial or non-bacterial in nature. Predominately, folliculitis is caused by gram positive organisms such as Staphylococcus and Streptococcus and less frequently by gram negative bacteria discussed hereinabove with respect to gram negative folliculitis.

Perioral dermatitis is a common papular inflammatory eruption which is confined around the mouth. It most commonly afflicts women in their early twenties to middle thirties, but it can be seen in adolescents and more mature adults.

Hiddradenitis suppurativa is a suppurative (chronic) and cystic disease of apocrine gland regions of the skin, including the axillae, perineum and groin.

There is a genetic tendency to acne, in particular acne congoblata which is a deep cystic and sinus forming type of acne. This condition is essentially a deep, aggressive form of cystic acne occurring in the apocrine gland regions. Topical administration of clindamycin has been used to treat this form of cystic acne.

The etiology of acne vulgaris and related disorders as discussed above is not completely known in every detail. However, what is known is that acne, in general, is caused by a plurality of factors. In general, there are four main factors that cause acne: genetics; hormonal activity; bacteria; and the inflammatory response.

Genetics is a prominent component as it is well known that several members of the same family can be affected with moderate to severe scarring acne. The inheritance by some is thought to be autosomal dominant, but this has not been definitively proven. Furthermore, on the molecular level, there has not yet been discovered a gene or group of genes that are responsible for the various forms of acne vulgaris.

Another key factor in the development of acne is hormonal. In adolescence, for example, it is thought that androgens can interact with receptors on the sebaceous glands and cause stimulation of the sebaceous gland, to hypertrophy and hence form more sebaceous production of lipids and free fatty acids which distend the follicular canal. More specifically, there is evidence for increased peripheral metabolic conversion of the androgen testosterone to dihydrotestosterone at the level of the skin in acne patients. It is further hypothesized that receptors on the sebaceous gland for the active androgen dihydrotestosterone can exhibit various degrees of sensitivity and that a heightened sensitivity response may be partially or entirely genetically predetermined.

Another causative factor in acne is the presence of bacteria in the follicular canal. Within the follicular canal are bacteria which are indigenous to the follicular lining. Among the bacteria flora present are anaerobic, gram positive organisms called Proprionibacterium acnes. It is interesting to note that they are present in abundance in pathologically affected sites. They are reduced during oral antimicrobial treatment and their absence from nonhuman animal skin is striking especially since animals do not exhibit acne vulgaris.

Yet another causative factor in acne is the inflammatory response manifested in the skin. More specifically, it is thought that Proprionibacterium acnes lives in symbiosis on the keratin lined follicular canal. Proprionibacterium acnes ingests the sebum produced from the sebocytes of the sebaceous glands. This nascent sebum is largely lipid in composition and also contains DNA, RNA, proteins and other cellular components that result from the breakdown of sebocytes themselves. The Proprionibacterium acnes which are highly lipophilic, feed on the nascent sebum. It has been shown that Proprionibacterium acnes are found only in sebaceous rich areas. If the nutrients increase due to an active and large sebaceous system, then colonization and high growth rates of Proprionibacterium acnes will form. It has been shown that the resident bacterial flora will produce biologically active molecules such as histamine, extracellular enzymes and peptides which may be responsible for the chemotaxis of the inflammatory infiltrate in acne vulgaris. Since the follicular lining in the pilosebaceous unit is intact, it has been theorized that if colonization of Proprionibacterium acnes occurs in sufficient numbers, they could produce initiating antigenic molecules that promote the initiation of inflammation. Proprionibacterium acnes can produce proteinases, lipase and hyaluronate lyase all of which may serve as the catalysts or initiators of the inflammatory infiltrate which has been shown to be composed of neutrophils and lymphocytes.

A number of treatments are presently known for treating acne, some more successful than others. Some modes of treatment have been mentioned above. There are two modes of treatment, topical and systemic.

Aside from treatments mentioned above, some additional systemic treatments for acne that are presently employed are: oral tetracycline; oral erythromycin; minocycline; doxycycline; oral trimethoprim-sulfamethoxazole and isotretinoin.

Some of the topical treatments that are presently employed are: topical erythromycin, clindamycin, benzoyl peroxide, 2% sulfur, 3% resorcinol, a tetracycline derivative (meclocycline sulfosalicylate 1%), 2% salicylic acid and tretinoin.

Topical treatments that have been suggested in the past and that are no longer generally employed include: x-ray treatment; electric sparks; vitamin therapy; and treatment with a plant extract as described in U.S. Pat. No. 4,803,069.

More specifically with respect to the topical use of certain specific antibiotics, topical solutions, ointments, creams and gels containing erythromycin, clindamycin or meclocycline sulfosalicylate 1% (a tetracycline derivative).

Some of the undesirable side effects of orally administered antibiotics are abdominal cramps, black tongue, cough, diarrhea, fatigue, irritation of the mouth, loss of appetite, nausea, vomiting, fever, hearing loss, jaundice, rash, rectal and vaginal itching and superinfection.

The etiopathology of acne, although unclear, starts in formation of a characteristic lesion: the comedo. This produces a blockage in the pilosebaceous canal following dyskeratinization of the infundibular zone of the canal. A major effect of the blockage is to modify the rheology of the sebum and the physicochemical properties of the area. Such modification allows resident cutaneous strains to hyperproliferate which in turn triggers an inflammation reaction in the organism.

Benzoyl peroxide has been known for several years to be a particularly interesting keratolytic agent among recognized therapeutic acne treatments. In addition, it has good bacteriostatic properties.

Use of standard antibiotics in acne treatment is also widespread. They do, in fact, shown considerable bacteriostatic and anti-inflammatory activity. Orally administered active antibiotics are numerous. Among these, clindamycin and especially erythromycin show topical activity.

Antibiotics have previously been combined with benzoyl peroxide in order to increase the activity of topical anti-acne compositions. In particular, erythromycin has already been combined with benzoyl peroxide (French patent no. 7,702, 157).

However, a major drawback of the use of antibiotics (either alone or in combination with benzoyl peroxide) lies in their prolonged use whereupon bacterial flora become resistant, rendering the antibiotics less effective in subsequent treatment. Further, benzoyl peroxide-erythromycin combinations are unstable over periods of time.

Especially in the treatment of patients with inflammatory lesions, benzoylperoxide is often used in combination with orally administered antibiotics, e.g. tetracycline, erythromycin and the like. However, many questions have been raised concerning the safety of short and long term use of orally administered antibiotics in the treatment of acne. Moreover, as a general rule, it is desirable to avoid oral therapy in the treatment of skin diseases whenever an effective topical treatment modality is available. Compositions, which are suitable for topical administration and which comprise benzoylperoxide in combination with, for example, erythromycin, are described in French Pat. No. 2,378,523. These compositions are known to reduce the numbers of Propionibacterium acnes, the main organism involved in the acne bearing areas.

SUMMARY OF THE INVENTION

The present invention is concerned with pharmaceutical compositions for the topical treatment of acne vulgaris, which compositions are not irritating and have, compared with those known in the art, an improved anti-acne activity. These compositions comprise a pharmaceutically acceptable inert carrier material and, as active ingredients, zinc oxide and a compound of the formula $C_6H_2ClOHR^1R^2$, wherein $R^1$ and $R^2$ are each independently C1 to C7 alkyl, C3 to C7 cycloalkyl or C3 to C7 aryl.

In the foregoing definitions the term "alkyl" is meant to include straight and branch chained hydrocarbon radicals having from 1 to 7 carbon atoms such as, for example, methyl, ethyl, propyl, isopropyl, butyl, pentyl, hexyl and the like. "Cycloalkyl" includes cyclic hydrocarbon radicals having from 3 to 7 carbon atoms, for example, cyclopropyl, cyclobutyl, cyclopentyl, cyclohexyl and cycloheptyl. "Aryl" refers to carbocyclic aromatic radicals having from 3 to 7 carbon atoms, for example, phenyl.

Preferred compositions according to the present invention are those wherein $R^1$ and $R^2$ are each C1 to C7 alkyl, either straight or branched chain.

More preferred are those compositions wherein $R^1$ and $R^2$ are each C1 to C3 alkyl.

Most preferred compositions are those wherein $R^1$ and $R^2$ are each methyl, that is, 4-chloro-3,5-dimethylphenol.

Because of their properties, compositions according to the invention are suitable for treatment of cutaneous disorders and dermatoses, such as acne in particular, cutaneous ulcers, warts and skin dyskeratinization.

An object of the present invention is therefore a topical pharmaceutical and cosmetic composition containing zinc oxide and a compound of the formula $C_6H_2ClOHR^1R^2$, which may be combined with binders, fillers and/or emulsifiers in an acceptable physiological support.

A further object of the invention concerns the method of use of the composition in the therapeutic treatment of acne.

A still further object of the invention is the provision of a composition and a method of cosmetic treatment.

It is an object of the present invention to provide topically applied pharmaceutical compositions suitable for the treatment of various ailments and physical conditions of the skin such as acne, bed sores, burns, infections, trauma, ulcers, wounds and wrinkles.

It is a further object to provide compositions of the type described which are more effective than compositions presently known in the art.

It is a prime object of the invention to provide topical compositions of the type described for the treatment of acne and more particularly, severe forms of acne, which compositions are more effective as remedies than the compositions presently known and used in the art.

Further objects of the invention will become apparent from the following description and examples.

The foregoing and other objects, advantages and characterizing features will become apparent from the following description of certain illustrative embodiments of the invention.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings.

BRIEF LIST OF REFERENCE NUMERALS UTILIZED IN THE DRAWINGS

Figure 1:
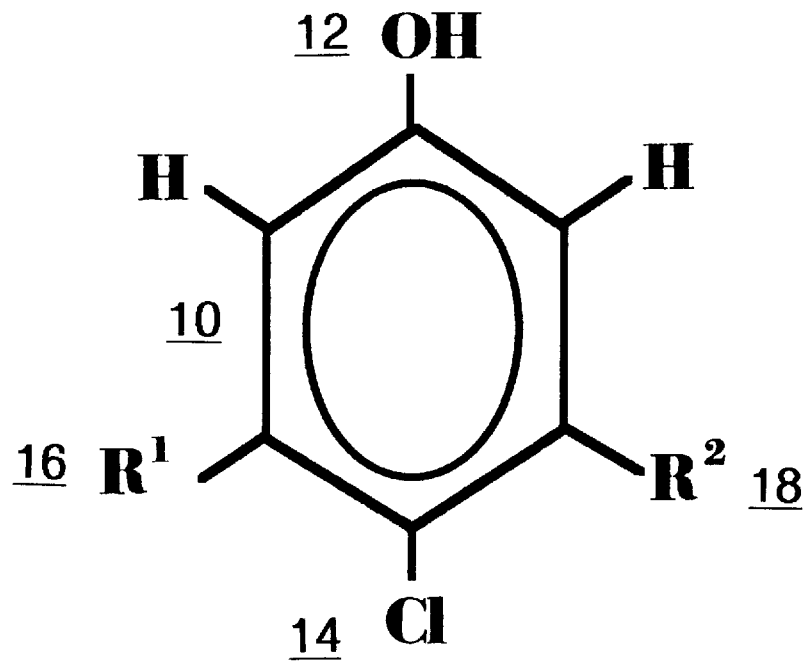
FIG. 1 is a structural view of the general class of compounds of the present invention, with the preferred groups for $R^1$ and $R^2$ shown.
Figure 2:
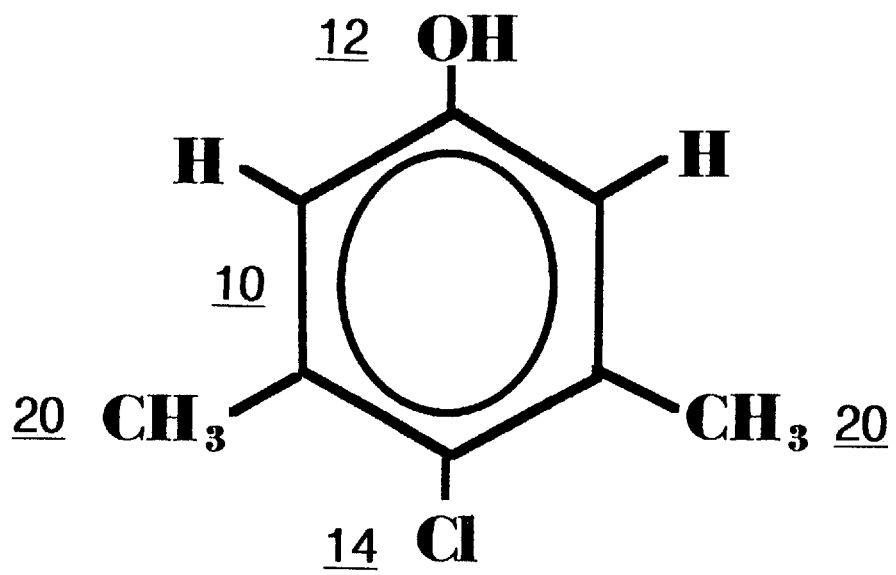
FIG. 2 is a structural view of the most preferred compound of the present invention, 4-chloro-3,5-dimethylphenol.
Figure 3:
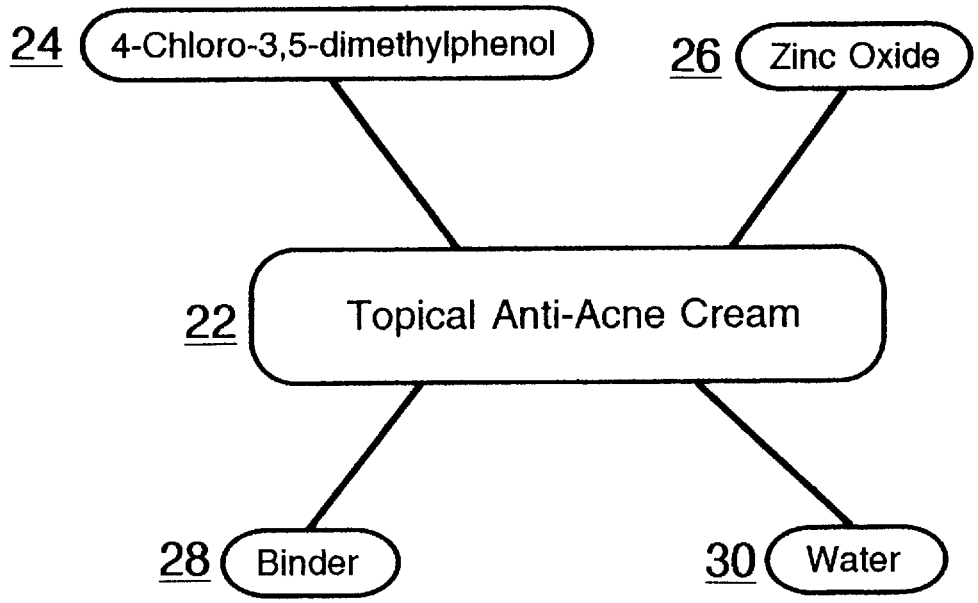
FIG. 3 is a flow diagram of the primary and secondary ingredients utilized in the formulation of the present invention.

10—compound of the formula $C_6H_2ClOHR^1R^2$
12—hydroxyl moiety
14—chloro moiety
16—$R^1$ moiety
18—$R^2$ moiety
19—definition of $R^1$ and $R^2$ as C1 to C7 alkyl, either straight or branched chain
20—methyl moieties which are the preferred units for $R^1$ and $R^2$
21—chemical name of the preferred compound, 4-chloro-3,5-dimethylphenol 22—general formulation for the topical anti-acne formulation of the present invention
24—the preferred compound, 4-chloro-3,5-dimethylphenol
26—zinc oxide
28—binder
30—water

DETAILED DESCRIPTION OF THE PREFERRED EMBODIMENT

In addition to the above-described active components, a topical formulation of the present invention must be in a pharmaceutically acceptable carrier. This carrier can include various other adjuncts, for example, binders, emollients such as cetyl alcohol and sperm was, dispersing agents such as stearyl alcohol and sodium lauryl sulfate, lubricants such as mineral oil, stabilizers such as bees wax, dyes and perfumes, suspending agents such as methocel, antibacterial agents such as methylparaben and propylparaben, antifoaming agents such as silicone, anti-irritants such as camphor, emulsifiers such as polyethylene lauryl ether, and absorption enhancers such as isopropyl myristate. With regard to the relative composition, zinc oxide will generally comprise from about 1 to about 5% of zinc oxide and from about 0.5 to about 3.0% of a compound of the formula $C_6H_2ClOHR^1R^2$.

EXAMPLE 1

By the method described below, a formulation of the following composition was prepared.

| | |
|---|---|
| Water, deionized | 60 wt. % |
| Cetyl alchol | 7.5 |
| Stearyl alcohol | 6.8 |
| Spermwax | 6.0 |
| Isopropyl myristate | 5.0 |
| Bees wax (white) | 2.5 |
| Polyethylene lauryl ether | 2.4 |
| 4-chloro-3,5-dimethylphenol | 2.25 |
| Mineral oil | 2.0 |
| Fragrance | 1.5 |
| Zinc oxide | 1.0 |
| Sodium lauryl sulfate | 1.0 |
| Camphor | 0.75 |
| Silicone | 0.50 |
| Methylparaben | 0.40 |
| Propylparaben | 0.20 |
| Methocel | 0.20 |

Step 1. Combine bees wax, stearyl alcohol, cetyl alcohol, 4-chloro-3,5-dimethylphenol, camphor, methylparaben, propylparaben, mineral oil, isopropyl myristate, polyethylene lauryl ether and spermwax. Heat to melt and mix well.

Step 2. Put 90% of the deionized water into a separate container, heat to 165° C. Add and dissolve the methocel.

Step 3. In the remaining 10% of the deionized water, add and dissolve the sodium lauryl sulfate and zinc oxide. Mix well and filter through Nitex nylon screen #3-85/35xx.

Step 4. Add the product of Step 3, above, to the product of Step 2, above, and mix well.

Step 5. Add the product of Step 4, above, to the product of Step 1, above. Mix well at about 1750 rpm.

Step 6. Cool the batch to 120° C. and add the fragrance. Mix well to dissolve.

Step 7. Add and dissolve the silicone.

Step 8. Cool the batch to room temperature and fill into appropriate containers.

It will be understood that each of the elements described above, or two or more together, may also find a useful application in other types of formulations differing from the type described above.

While the invention has been illustrated and described as embodied in a topical anti-acne formulation, it is not intended to be limited to the details shown, since it will be understood that various omissions, modifications, substitutions and changes in the forms and details of the formulation illustrated and in its operation can be made by those skilled in the art without departing in any way from the spirit of the present invention.

Without further analysis, the foregoing will so fully reveal the gist of the present invention that others can, by applying current knowledge, readily adapt it for various application without omitting features that, from the standpoint of prior art, fairly constitute essential characteristics of this invention.

What is claimed as new and desired to be protected by Letters Patent is set forth in the appended claims:

1. A topical anti-acne formulation comprising the following ingredients:

| | |
|---|---|
| Water, deionized | 60 wt. %; |
| Cetyl alcohol | 7.5; |
| Stearyl alcohol | 6.8; |
| Spermwax | 6.0; |
| Isopropyl myristate | 5.0; |
| Bees was (white) | 2.5; |
| Polyethylene lauryl ether | 2.4; |
| 4-chloro-3,5-dimethylphenol | 0.5 to 3.0; |
| Mineral oil | 2.0; |
| Fragrance | 1.5; |
| Zinc oxide | 1.0 to 5.0; |
| Sodium lauryl sulfate | 1.0; |
| Camphor | 0.75; |
| Silicone | 0.50; |
| Methylparaben | 0.40; |
| Propylparaben | 0.20; and |
| Methocel | 0.20. |

\* \* \* \* \*